United States Patent [19]
Jensen-Korte et al.

[11] Patent Number: 4,820,725
[45] Date of Patent: Apr. 11, 1989

[54] 1-ARYL-PYRAZOLES, PESTICIDAL COMPOSITIONS AND USE

[75] Inventors: Uta Jensen-Korte, Duesseldorf; Reinhold Gehring, Wuppertal; Otto Schallner, Monheim; Jörg Stetter, Wuppertal; Heinz-Jürgen Wroblowsky, Langenfeld; Benedikt Becker, Mettmann; Wilhelm Stendel, Wuppertal; Berhard Homeyer, Leverkusen; Wolfgang Behrenz, Overath, all of Fed. Rep. of Germany

[73] Assignee: Bayer Aktiengesellschaft, Leverkusen, Fed. Rep. of Germany

[21] Appl. No.: 893,133

[22] Filed: Aug. 4, 1986

[30] Foreign Application Priority Data

Aug. 21, 1985 [DE] Fed. Rep. of Germany ....... 3529829

[51] Int. Cl.$^4$ .................... A01N 43/56; C07D 231/18
[52] U.S. Cl. .................... 514/407; 514/341; 546/279; 548/375; 548/376; 548/377
[58] Field of Search ...................... 548/375, 376, 377; 546/279; 514/407, 341

[56] References Cited

U.S. PATENT DOCUMENTS 4,008,249  2/1977  Fischer et al. ...................... 548/377

FOREIGN PATENT DOCUMENTS 0025859  4/1981  European Pat. Off. .
0138527  4/1985  European Pat. Off. .
0151866  8/1985  European Pat. Off. .
2409753  9/1975  Fed. Rep. of Germany .
2839270  3/1980  Fed. Rep. of Germany .
2073172  10/1981  United Kingdom .

OTHER PUBLICATIONS

Cowell et al., J. Chem. Soc., 1963, pp. 4920–4924.

Primary Examiner—Robert W. Ramsuer
Attorney, Agent, or Firm—Sprung Horn Kramer & Woods

[57] ABSTRACT

1-Aryl-pyrazole of the formula $$\begin{array}{c} R^1 \text{—} \boxed{\phantom{xxx}} \text{—} S(O)_n \text{—} R^2 \\ N \diagdown \phantom{xx} \diagup R^3 \\ N \\ | \\ Ar \end{array}$$

in which
 $R^1$ represents hydrogen, alkyl or halogenoalkyl,
 $R^2$ represents alkyl, halogenoalkyl or in each case optionally substituted aralkyl or aryl,
 $R^3$ represents hydrogen or halogen,
 Ar represents optionally substituted phenyl or pyridyl, and
 n represents the number 0, 1 or 2, the 1-aryl-pyrazole being useful in agents for combating pests.

10 Claims, No Drawings

1-ARYL-PYRAZOLES, PESTICIDAL COMPOSITIONS AND USE

The invention relates to new 1-arylpyrazoles, a process for their preparation and their use as agents for combating pests, in particular as insecticides and acaricides.

It is already known that certain pyrazole derivatives, such as, for example, 1-cyclohexyl-5-[N,N-(dimethyl)-carbamoyloxy]-3-methylthiomethyl-pyrazole or 1-cyclohexyl-5-[N,N-(dimethyl)-carbamyloxy]-3-methyl-sulphonyl-methyl-pyrazole, have an insecticidal, nematicidal and fungicidal action.

The level of action and duration of action of these compounds, however, are not always completely satisfactory in all fields of use, especially against certain insects or when low concentrations are applied.

New 1-aryl-pyrazoles of the general formula (I)

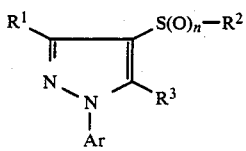

in which
R$^1$ represents hydrogen, alkyl or halogenoalkyl,
R$^2$ represents alkyl, halogenoalkyl or in each case optionally substituted aralkyl or aryl,
R$^3$ represents hydrogen or halogen,
Ar represents optionally substituted phenyl or pyridyl and
n represents the number 0, 1 or 2,
have now been found.

It has furthermore been found that the new 1-aryl-pyrazoles of the general formula (I)

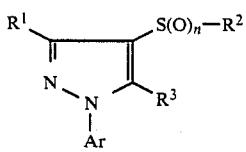

in which
R$^1$ represents hydrogen, alkyl or halogenoalkyl,
R$^2$ represents alkyl, halogenoalkyl or in each case optionally substituted aralkyl or aryl,
R$^3$ represents hydrogen or halogen,
Ar represents optionally substituted phenyl or pyridyl and
n represents the number 0, 1 or 2,
are obtained by a process in which 5-amino-1-aryl-pyrazoles of the formula (II)

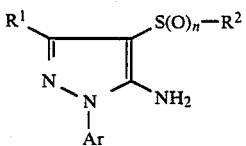

in which R$^1$, R$^2$, Ar and n have the abovementioned meaning, are reacted with an inorganic or organic nitrite in the presence of a reaction auxiliary, and if appropriate in the presence of a hydrogen halide acid and if appropriate in the presence of a diluent.

Finally, it has been found that the new 1-aryl-pyrazoles of the general formula (I) have insecticidal and acaricidal properties.

Surprisingly, 1-arylpyrazoles of the general formula (I) according to the invention exhibit a considerably better insecticidal and acaricidal activity than the pyrazole derivatives known from the prior art, such as, for example, 1-cyclohexyl-5-[N,N-(dimethyl)-carbamyloxy]-3-methylthiomethyl-pyrazole or 1-cyclohexyl-5-[N,N-(dimethyl)-carbamyloxy]-3-methylsulphonyl-methyl-pyrazole, which are closely related compounds chemically and from the point of view of their action.

Formula (I) provides a general definition of the 1-aryl-pyrazoles according to the invention. Preferred compounds of the formula (I) are those
in which
R$^1$ represents hydrogen, or represents in each case straight-chain or branched alkyl or halogenoalkyl with 1 to 4 carbon atoms and, where appropriate, 1 to 9 identical or different halogen atoms,
R$^2$ represents in each case straight-chain or branched alkyl or halogenoalkyl with in each case 1 to 8 carbon atoms and, where appropriate, 1 to 17 identical or different halogen atoms, or represents phenylalkyl or phenyl with, where appropriate, 1 to 4 carbon atoms in the straight-chain or branched alkyl part and in each case optionally monosubstituted or polysubstituted by identical or different substituents, possible substituents on the phenyl in each case being: halogen, cyano, nitro and in each case straight-chain or branched alkyl, alkoxy, alkylthio, alkylsulphinyl, alkylsulphonyl, halogenoalkyl, halogenoalkoxy, halogenoalkylthio, halogenoalkylsulphinyl and halogenoalkylsulphonyl with in each case 1 to 4 carbon atoms in the individual alkyl parts and, where appropriate, 1 to 9 identical or different halogen atoms,
R$^3$ represents hydrogen, fluorine, chlorine, bromine or iodine,
Ar represents phenyl, 2-pyridyl, 3-pyridyl or 4-pyridyl, optionally monosubstituted or polysubstituted by identical or different substituents, possible substituents in each case being: cyano, nitro, halogen, in each case straight-chain or branched alkyl, alkoxy and alkoxycarbonyl with in each case 1 to 4 carbon atoms and in each case straight-chain or branched halogenoalkyl or halogenoalkoxy with in each case 1 to 4 carbon atoms and 1 to 9 identical or different halogen atoms, and a radical —S(O)$_m$—R$^4$, wherein R$^4$ represents amino, or represents in each case straight-chain or branched alkyl, alkylamino, dialkylamino or halogenoalkyl with in each case 1 to 4 carbon atoms in the individual alkyl parts and, in the case of the halogenoalkyl, with 1 to 9 identical or different halogen atoms, m represents the number 0, 1 or 2 and n represents the number 0, 1 or 2.

Particularly preferred 1-arylpyrazoles of the formula (I) are those
in which
R$^1$ represents hydrogen, methyl, ethyl, n- or i-propyl or trifluoromethyl,
R$^2$ represents methyl, ethyl, n- or i-propyl, n-, i-, s- or t-butyl, n- or i-pentyl, n- or i-hexyl, chloromethyl, difluoromethyl, difluorochloromethyl, fluorodichloromethyl, trifluoromethyl, pentafluoroethyl, pentachloroethyl, fluorotetrachloroethyl, difluorotrichloroethyl, trifluorodichloroethyl, tetrafluorochloroethyl, heptafluoropropyl, chloroethyl, bromoethyl, chloropropyl or bromopropyl, or represents phenyl, benzyl or phenethyl, in each case optionally mono-, di- or tri-substituted by identical or different substituents, possible substituents on the phenyl being: fluorine, chlorine, bromine, iodine, cyano, nitro, methyl, ethyl, methoxy, methylthio, trifluoromethyl, methylsulphinyl, methylsulphonyl, trifluoromethoxy, trifluoromethylthio, trifluoromethylsulphinyl or trifluoromethylsulphonyl, R³ represents hydrogen, fluorine, chlorine or bromine, Ar represents phenyl which is optionally mono-, di-, tri-, tetra- or pentasubstituted by identical or different substituents, or represents 2-pyridyl or 4-pyridyl, in each case optionally mono-, di-, tri- or tetrasubstituted by identical or different substituents, possible substituents on the phenyl or pyridyl in each case being: cyano, nitro, fluorine, chlorine, bromine, iodine, methyl, ethyl, n- and i-propyl, n-, i-, s- and t-butyl, methoxy, ethoxy, methoxycarbonyl, ethoxycarbonyl, trifluoromethyl, trichloromethyl, dichlorofluoromethyl, difluorochloromethyl, chloromethyl, dichloromethyl, difluoromethyl, pentafluoroethyl, tetrafluoroethyl, trifluorochloroethyl, trifluoroethyl, difluorodichloroetyl, trifluorodichloroethyl, pentachloroethyl, trifluoromethoxy, trifluoromethoxy, dichlorofluoromethoxy, difluorochloromethoxy, chloromethoxy, dichloromethoxy, difluoromethoxy, pentafluoroethoxy, tetrafluoroethoxy, trifluorochloroethoxy, trifluoroethoxy, difluorodichloroethoxy, trifluorodichloroethoxy, pentachloroethoxy and a radical —S(O)$_m$—R⁴, wherein R⁴ represents amino, methylamino, ethylamino, dimethylamino, diethylamino, fluorodichloromethyl, difluorochloromethyl, tetrafluoroethyl, trifluorochloroethyl, trifluoromethyl, methyl or ethyl, m represents the number 0, 1 or 2 and n represents the number 0, 1 or 2.

The following 1-arylpyrazoles of the general formula (I) may be mentioned specifically, in addition to the compounds mentioned in the preparation examples:

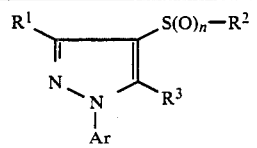

| R¹ | R² | R³ | n | Ar |
|---|---|---|---|---|
| H | —CF₂Cl | H | 0 | 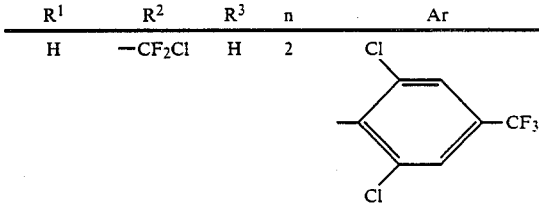 |
| H | —CF₂Cl | H | 1 | 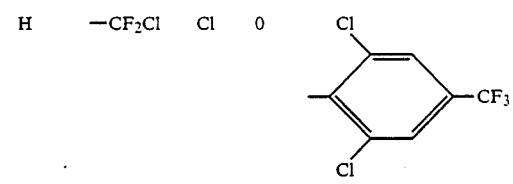 |
| H | —CF₂Cl | H | 2 | 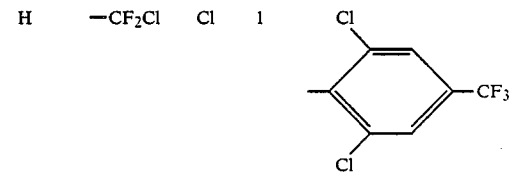 |
| H | —CF₂Cl | Cl | 0 | 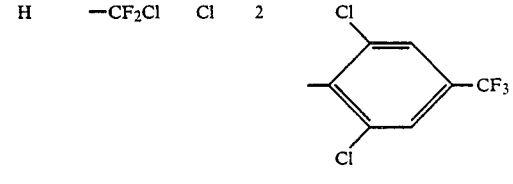 |
| H | —CF₂Cl | Cl | 1 | 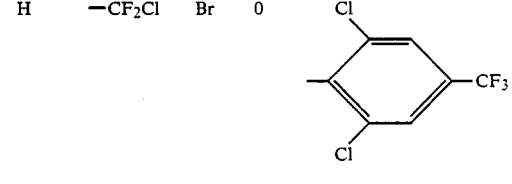 |
| H | —CF₂Cl | Cl | 2 | 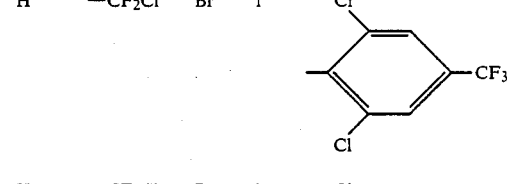 |
| H | —CF₂Cl | Br | 0 | 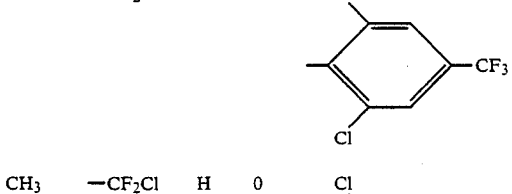 |
| H | —CF₂Cl | Br | 1 | |
| H | —CF₂Cl | Br | 2 | |
| CH₃ | —CF₂Cl | H | 0 |  |

-continued
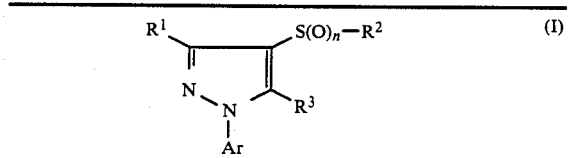    (I)
| R¹ | R² | R³ | n | Ar |
|---|---|---|---|---|
| CH₃ | —CF₂Cl | H | 1 | 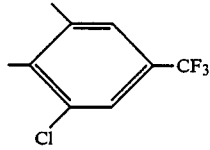 |
| CH₃ | —CF₂Cl | H | 2 | 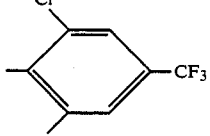 |
| CH₃ | —CF₂Cl | Cl | 0 | 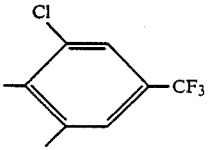 |
| CH₃ | —CF₂Cl | Br | 0 | 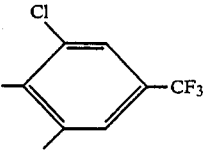 |
| H | —CF₃ | H | 0 | 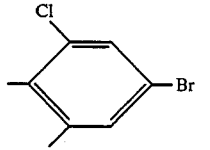 |
| H | —CF₃ | H | 2 | 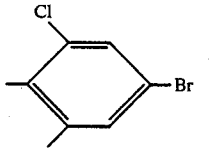 |
| H | —CF₃ | Cl | 0 | 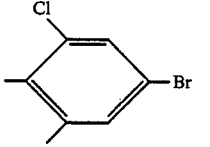 |
| H | —CF₃ | Cl | 2 | 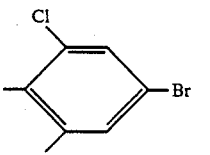 |
-continued
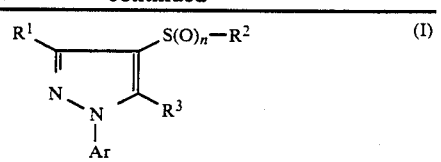    (I)
| R¹ | R² | R³ | n | Ar |
|---|---|---|---|---|
| H | —CF₃ | Br | 0 | 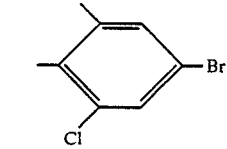 |
| H | —CF₃ | Br | 2 | 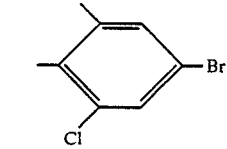 |
| H | —CF₂Cl | H | 0 | 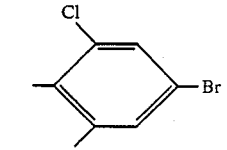 |
| H | —CF₂Cl | H | 1 | 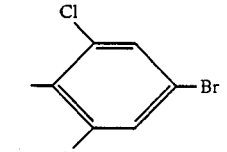 |
| H | —CF₂Cl | H | 2 | 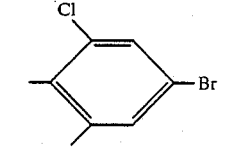 |
| H | —CF₂Cl | Cl | 0 | 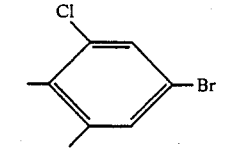 |
| H | —CF₂Cl | Cl | 2 | 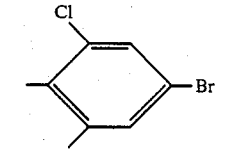 |
| H | —CF₂Cl | Br | 2 | 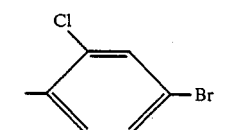 |

-continued $$\text{(I)}$$

Structure: pyrazole with R¹ at 3-position, S(O)ₙ-R² at 4-position, R³ at 5-position, and Ar on N1.

| R¹ | R² | R³ | n | Ar |
|---|---|---|---|---|
| CH₃ | —CF₃ | Cl | 0 | 2,5-dichloro-4-bromophenyl |
| CH₃ | —CF₃ | H | 0 | 2,5-dichloro-4-bromophenyl |
| CH₃ | —CF₃ | H | 1 | 2,5-dichloro-4-bromophenyl |
| CH₃ | —CF₃ | H | 2 | 2,5-dichloro-4-bromophenyl |
| CH₃ | —CF₂Cl | H | 0 | 2,5-dichloro-4-bromophenyl |
| CH₃ | —CF₂Cl | H | 1 | 2,5-dichloro-4-bromophenyl |
| CH₃ | —CF₂Cl | H | 2 | 2,5-dichloro-4-bromophenyl |
| CH₃ | —CF₂Cl | Cl | 0 | 2,5-dichloro-4-bromophenyl |
| CH₃ | —CF₂Cl | Br | 0 | 2,5-dichloro-4-bromophenyl |
| CH₃ | —CCl₂F | H | 0 | 2,5-dichloro-4-bromophenyl |
| CH₃ | —CCl₂F | H | 1 | 2,5-dichloro-4-bromophenyl |
| CH₃ | —CCl₂F | H | 2 | 2,5-dichloro-4-bromophenyl |
| CH₃ | —CCl₂F | Cl | 0 | 2,5-dichloro-4-bromophenyl |
| CH₃ | —CCl₂F | Br | 0 | 2,5-dichloro-4-bromophenyl |
| H | H | H | 0 | 2,5-dichloro-4-(trifluoromethyl)phenyl |
| H | CH₃ | H | 1 | 2,5-dichloro-4-(trifluoromethyl)phenyl |

-continued

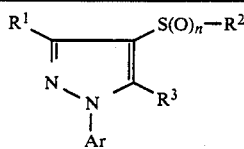

| R¹ | R² | R³ | n | Ar |
|---|---|---|---|---|
| H | CH₃ | H | 2 | 2,4-dichlorophenyl with CF₃ |
| H | CH₃ | Cl | 0 | 2,4-dichlorophenyl with CF₃ |
| H | CH₃ | Br | 0 | 2,4-dichlorophenyl with CF₃ |
| H | CH₃ | Cl | 0 | 2-chloro-4-bromophenyl |
| H | CH₃ | Br | 0 | 2-chloro-4-bromophenyl |

If, for example, 5-amino-4-dichlorofluoromethylsulphenyl-1-(2,6-dichloro-4-trifluoromethyl-phenyl)-pyrazole is used as the starting substance and sodium nitrite/hydrobromic acid are used as reagents, the course of the reaction in the process according to the invention can be represented by the following equation:

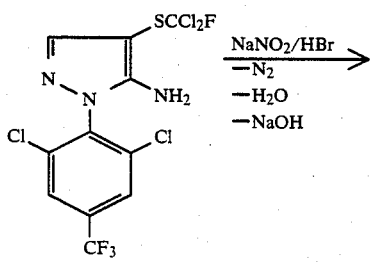

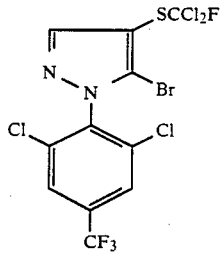

Formula (II) provides a general definition of the 5-amino-1-aryl-pyrazoles required as starting substances for carrying out the process according to the invention. In this formula (II), R¹, R², Ar and n preferably represent those radicals which have already been mentioned as preferred for these substituents and indices in connection with the description of the substances of the formula (I) according to the invention.

The 5-amino-1-aryl-pyrazoles of the formula (II) are the subject of commonly assigned application Ser. No. 690,347, filed Jan. 10, 1985, now pending and Ser. No. 858,475, filed Apr. 30, 1986, now pending, corresponding to German Patent Application Nos. P 3 402 308 and 3 517 843.

They are obtained by a process in which 4-thiocyanato-5-aminopyrazoles of the general formula (III)

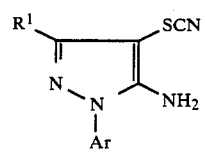

in which R¹ and Ar have the abovementioned meaning, or bis-(pyrazolyl) disulphides of the formula (IV)

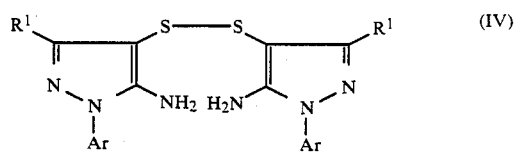

in which R¹ and Ar have the abovementioned meaning, are reacted with halides of the formula (V)

in which
R² has the abovementioned meaning and
Hal¹ represents halogen, in particular chlorine, bromine or iodine,
if appropriate in the presence of a diluent, such as, for example, methanol or ethanol, and if appropriate in the presence of a reducing agent, such as, for example, sodium borohydride or sodium dithionite, and if appropriate in the presence of a base, such as, for examle, sodium hydroxide or potassium carbonate, at temperatures between 20° C. and 90° C., or in which 4-unsubstituted 5-aminopyrazoles of the formula (VI)

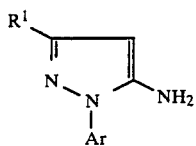 (VI)

in which $R^1$ and Ar have the abovementioned meaning, are reacted with sulphenyl halides of the formula (VII)

 (VII)

in which $R^2$ has the abovementioned meaning and $Hal^2$ represents halogen, in particular fluorine, chlorine, bromine or iodine, if appropriate in the presence of a diluent, such as, for example, methylene chloride, and if appropriate in the presence of an acid-binding agent, such as, for example, pyridine, at temperatures between 0° C. and 50° C., and, if appropriate, the 5-amino-pyrazoles thus obtained, of the formula (IIa)

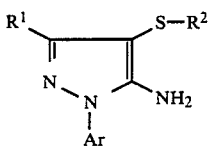 (IIa)

in which $R^1$, $R^2$ and Ar have the abovementioned meaning, are then oxidized on the sulphur of the sulphenyl group in the 4-position of the pyrazole ring with oxidizing agents of the formula (VIII)

R—O—OH (VIII)

in which R represents hydrogen, or represents in each case optionally substituted alkanoyl or aroyl, and preferably represents hydrogen, or represents acetyl, or represents propionyl, or represents trifluoroacetyl, or represents optionally substituted benzoyl, such as, for example, 3-chlorobenzoyl or 4-nitrobenzyl, if appropriate in the presence of a diluent, such as, for example, methylene chloride, if appropriate in the presence of a catalyst, such as, for example, ammonium molybdate, and if appropriate in the presence of an acid-binding agent, such as, for example, sodium carbonate or sodium bicarbonate, at temperatures between 0° C. and 50° C.

The 4-thiocyanato-5-aminopyrazoles of the formula (III) are known in some cases (compare, for example, Farmaco Ed. Sci. 38, 274–282 (1983). They are obtained, for example, by a process in which 4-unsubstituted 5-aminopyrazoles of the formula (VI)

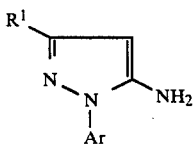 (VI)

in which $R^1$ and Ar have the abovementioned meaning, are reacted with ammonium thiocyanate in the presence of bromine and acetic acid at temperatures between −20° C. and +20° C.

The bis-(pyrazole) disulphides of the formula (IV) are not yet known. They are obtained by a process in which the 4-thiocyanato-5-amino-pyrazoles described above, of the formula (III), are reacted with aqueous hydrochloric acid, if appropriate in the presence of a diluent, such as, for example, ethanol, at temperatures between 20° C. and 120° C.

The halides of the formula (V) are generally known compounds of organic chemistry.

The 4-unsubstituted 5-aminopyrazoles of the formula (VI) are known in some cases (compare, for example, J. Org. Chem. 36, 2972–2974 (1971) or J. Hetero-cyclic Chemistry 7, 345–349 (1970); and C.A. 62: 13137c).

They are obtained, for example, by a process in which arylhydrazines of the formula (IX)

Ar—NH—NH$_2$ (IX)

in which Ar has the abovementioned meaning, are either initially reacted in a 1st stage with acrylonitrile derivatives of the formula (X)

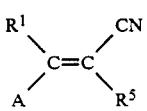 (X)

in which $R^1$ has the abovementioned meaning, $R^5$ represents hydrogen or alkoxycarbonyl and A represents halogen, hydroxyl, alkoxy, amino or dialkylamino, if appropriate in the presence of a diluent, such as, for example, ethanol or glacial acetic acid, and if appropriate in the presence of a reaction auxiliary, such as, for example, sodium acetate, at temperatures between −20° C. and +20° C., to give the arylhydrazine derivatives of the formula (XI)

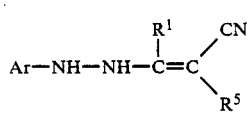 (XI)

in which Ar, $R^1$ and $R^5$ have the abovementioned meaning, and these are cyclized in a 2nd stage, if appropriate in the presence of a diluent, such as, for example, ethylene glycol monoethyl ether, at temperatures between +50° C. and +150° C., or are cyclized directly in one reaction step, without isolation of the intermediate stage of the formula (XI), if appropriate in the presence of a diluent, such as, for example, ethylene glycol monoethyl ether, at temperatures between +50° C. and +150° C., directly to give the 5-aminopyrazoles of the formula (VIa)

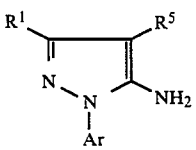 (VIa)

in which $R^1$, $R^5$ and Ar have the abovementioned meaning, and, in the case where $R^5$ represents alkoxycarbonyl, the compounds of the formula (VIa) are hydrolyzed and decarboxylated in the generally customary manner, if appropriate in the presence of a diluent, such as, for example, ethanol or isopropanol, and if appropriate in the presence of a catalyst, such as, for example, hydrobromic acid, at temperatures between 50 ° C. and 150° C.

The arylhydrazines of the formula (IX) are known (compare, for example, U.S. Pat. No. 4,127,575; U.S. Pat. No. 3,609,158; DE-OS (German Published Specification) No. 2,558,399; and J. Chem. Soc. C, 1971, 167–174), or they can be prepared by processes which are known in principle, in a simple analogous manner (compare Houben-Weyl "Methoden der organischen Chemie" ("Methods of Organic Chemistry") Volume X, 2 page 203, Thieme Verlag Stuttgart 1967).

The acrylonitrile derivatives of the formula (X) are generally known compounds of organic chemistry.

The sulphenyl halides of the formula (VII) are generally known compounds of organic chemistry.

The oxidizing agents of the formula (VIII) are likewise generally known compounds of organic chemistry.

Possible diluents for carrying out the process according to the invention are all the solvents which are usually customary for such diazotization reactions. Solvents which are preferably used are hydrocarbon halides, such as chloroform or bromoform, or aqueous acids, such as, for example, hydrogen halide acids or sulphuric acid, the acid component simultaneously functioning as the reagent and/or as the reaction auxiliary. If bromoform is used as the diluent, as a rule the corresponding 5-bromo-pyrazoles are obtained, bromoform simultaneously functioning as the diluent and as the reagent.

The corresponding reaction in the presence of chloroform as the diluent in general gives a mixture of 5-chloro-pyrazole compounds of the formula (I) and the analogous reduced compounds of the formula (I) which carry a hydrogen radical in the 5-position of the pyrazole ring. These mixtures can be separated by distillation.

The process according to the invention is carried out in the presence of an inorganic or organic nitrite. Possible nitrites are all the nitrite compounds usually customary for such diazotization reactions. Nitrites which are particularly preferably used are alkali metal nitrites, such as, for example, sodium nitrite, or alkyl nitrites, such as, for example, t-butyl nitrite.

If appropriate, the process according to the invention is carried out in the presence of a hydrogen halide acid. In this case, 1-aryl-pyrazoles of the formula (I) in which the radical $R^3$ represents a halogen radical corresponding to the anion of the hydrogen halide acid used are obtained as reaction products. In each case aqueous solutions of hydrofluoric acid, hydrochloric acid, hydrobromic acid or hydriodic acid are preferably used.

The process according to the invention is usually carried out in the presence of a reaction auxiliary. Possible reaction auxiliaries are, in particular, strong mineral acids, such as sulphuric acid or phosphoric acid, or the abovementioned hydrogen halide acids, which in this case simultaneously act as the reagent and as the catalyst.

If appropriate, the process according to the invention can be carried out in the presence of a suitable reducing agent. In this case, 1-aryl-pyrazoles of the formula (I) in which the radical $R^3$ represents hydrogen are obtained as reaction products. The reducing agent which is particularly preferably used in these cases is hypophosphorous acid ($H_3PO_2$).

The reaction temperatures can be varied within a substantial range in carrying out the process according to the invention. The reaction is in general carried out at temperatures between $-30°$ C. and $+60°$ C., preferably at temperatures between $-20°$ C. and $+40°$ C.

For carrying out the process according to the invention, in general 1.0 to 1.8 moles of nitrite, if appropriate 1.0 to 20.0 moles, preferably 1.0 to 10.0 moles, of hydrogen halide acid, if appropriate 1.0 to 50.0 moles, preferably 1.0 to 20.0 moles, of reducing agent and if appropriate 1.0 to 20.0 moles, preferably 1.0 to 10.0 moles, of mineral acid used as a reaction auxiliary are employed per mole of 5-amino-1-aryl-pyrazole of the formula (II).

The nitrite is usually added here in small portions, if appropriate dissolved in a suitable diluent, to the reaction mixture consisting of 5-amino-1-aryl-pyrazole of the formula (II), mineral acid, diluent and hydrogen halide acid or reducing agent.

The reaction products of the formula (I) are worked up and isolated by customary methods, for example by filtering off crystalline products or by extraction with a suitable organic solvent. Identification is by the melting point or proton nuclear magnetic resonance spectrum.

Alternatively, compounds of the formula (Ia) according to the invention

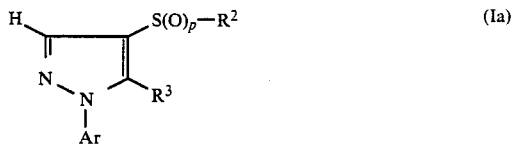

in which $R^2$ and Ar have the abovementioned meaning and p represents the number 1 or 2, are obtained from the compounds of the formula (Ib) according to the invention

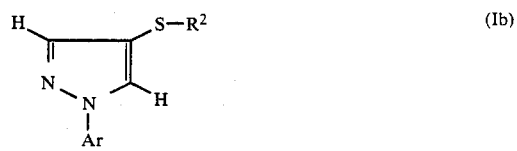

in which $R^2$ and Ar have the abovementioned meaning, by a process in which oxidation is carried out on the sulphur of the sulphenyl group in the 4-position of the pyrazole ring in the customary manner with oxidizing agents of the formula (VIII)

R—O—OH                                    (VIII)

in which R represents hydrogen, or represents in each case optionally substituted alkanoyl or aroyl, and in particular represents hydrogen, or represents acetyl, propionyl or trifluoroacetyl, or represents optionally substituted benzoyl, such as, for example, 3-chlorobenzoyl or 4-chlorobenzoyl, if appropriate in the presence of a diluent, such as, for example, methylene chloride, and if appropriate in the presence of a catalyst, such as, for example, ammonium molybdate, and if appropriate in the presence of an acid-binding agent, such as, for example, sodium carbonate or sodium bicarbonate, at temperatures between 0° and 50° C. (compare also the preparation examples).

The active compounds are well tolerated by plants, have a favorable level of toxicity to warm-blooded animals, and are suitable for combating animal pests, especially insects, arachnida and nematodes, which are encountered in agriculture, in forestry, in the protection of stored products and of materials, and in the hygiene field. They are active against normally sensitive and resistant species and against all or some stages of development. The abovementioned pests include:

From the order of the Isopoda, for example, *Oniscus asellus, Armadillidium vulgare* and *Porcellio scaber*. From the order of the Diplopoda, for example, *Blaniulus guttulatus*. From the order of the Chilopoda, for example, *Geophilus carpophagus* and *Scutigera spec*. From the order of the Symphyla, for example, *Scutigerella immaculata*. From the order of the Thysanura, for example, *Lepisma saccharina*. From the order of the Collembola, for example, *Onychiurus armatus*. From the order of the Orthoptera, for example, *Blatta orientalis, Periplaneta americana, Leucophaea maderae, Blattella germanica, Acheta domesticus,* Gryllotalpa spp., *Locusta migratoria migratorioides, melanoplus differentialis* and *Schistocerca gregaria*. From the order of the Dermaptera, for example, *Forficula auricularia*. From the order of the Isoptera, for example, Reticulitermes spp. From the order of the Anoplura, for example *Phylloxera vastatrix*, Pemphigus spp., *Pediculus humanus corporis*, Haematopinus spp. and Linognathus spp. From the order of the Mallophaga, for example, Trichodectes spp. and Damalinea spp. From the order of the Thysanoptera, for example, *Hercinothrips femoralis* and *Thrips tabaci*. From the order of the Heteroptera, for example, Eurygaster spp., *Dysdercus intermedius, Piesma quadrata, Cimex lectularius, Rhodnius prolixus* and Triatoma spp. From the order of the Homoptera, for example, *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma Lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata Lugens, Aonidiella aurantii, Aspidiotus hederae,* Pseudococcus spp. and Psylla spp. From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia Litura,* Spodoptera spp., *Trichoplusia ni, Carpocapsa pomonella,* Pieris spp., Chils spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana*. From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica*. From the order of the Hymenoptera, for example, Diprion spp., Hoplocampa spp., Lasius spp., *Monomorium pharaonis* and Vespa spp. From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp, Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa*. From the order of the Siphonaptera, for example, *Xenopsylla cheopis* and Ceratophyllus spp. From the order of the Arachnida, for example, *Scorpio maurus* and *Latrodectus mactans*. From the order of the Acarina, for example, *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chlorioptes spp., Sarcoptes spp., Tarsonemus spp., *Bryobia praetiosa,* Panonychus spp. and Tetranychus spp.

The active compounds according to the invention have an action not only against plant pests, hygiene pests and pests of stored products, but also in the field of veterinary medicine against animal parasites (ectoparasites), such as scale ticks, leather ticks, hunting mites, chiggers, flies (biting and licking), parasitic fly larvae, lice, hair lice, feather lice and fleas.

They are active against normally sensitive and resistant species and strains, and against all parasitic and non-parasitic develpment stages of the ectoparasites.

The active compounds according to the invention are distinguished by a powerful insecticidal and acaricidal activity. They can be used with particularly good success against insects which damage plants, such as, for example, against the larvae of the mustard beetle (*Phaedon cochleariae*) and against mites which damage plants, such as, for example, against the common spider mite (*Tetranychus urticae*). In addition, they are also outstandingly suitable for combating soil insects and can be used, for example, for combating *Phorbia antiqua* grubs.

The active compounds according to the invention furthermore have a powerful action against hygiene pests and pests of stored products, and can be used, for example, for combating the house fly (*Musca domestica*), for combating the common corn weevil (*Sitophilus granarius*) or for combating the Madeira cockroach (*Leucophaea maderae*). The active compounds according to the invention can moreover be used with particularly good success for combating warmblooded pests which live as parasites, such as, for example, against the larvae of the gold fly (*Lucilia cuprina*) or against biting flies (*Stomoxys calcitrans*). The active compounds according to the invention also have a good fungicidal activity when applied in corresponding amounts, and can be used, for example, for combating Botrytis and Venturia species.

The active compounds can be converted to the customary formulations, such as solutions, emulsions, suspensions, powders, foams, pastes, granules, aerosols, natural and syntheteic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylenefatty alcohol ethers, for example alkylaryl polyglycol ethers, alkyl sulphonates, alkyl sulphates, aryl sulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules and latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in their commercially available formulations and in the use forms, prepared from these formulations, as a mixture with other active compounds, such as insecticides, baits, sterilizing agents, acaricides, nematicides, fungicides, growth-regulating substances or herbicides. The insecticides include, for example, phosphates, carbamates, carboxylates, chlorinated hydrocarbons, phenylureas, substances produced by microorganisms.

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compounds are distinguished by an excellent residual action on wood and clay as well as a good stability to alkali on limed substrates.

The active compounds which can be used according to the invention are also suitable for combating insects, mites, ticks and the like in the field of livestock husbandry and animal breeding, it being possible to achieve better results, for example higher milk yields, a heavier weight, a more attractive animal coat, a longer life and the like, by combating the pests.

The active compounds according to the invention are used in a known manner in this field, such as by oral administration, for example in the form of tablets, capsules, drinks and granules, by dermal application, for example in the form of dipping, spraying, pouring on and spotting on, and dusting, and by parenteral administration, for example in the form of an injection, and furthermore by the "feed-through" method. Use in the form of shaped articles (neck collar or ear tag) is furthermore also possible.

The biological activity of the compounds according to the invention may be illustrated with the aid of the following examples.

PREPARATION EXAMPLES

Example 1

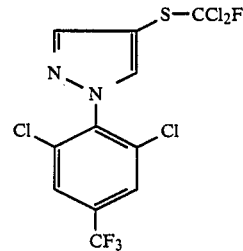

15 g (0.035 mole) of 5-amino-4-dichlorofluoromethylmercapto-1-(2,6-dichloro-4-trifluoromethylphenyl)-pyrazole are dissolved in a mixture of 100 ml of glacial acetic acid and 35 ml of 85% strength phosphoric acid, and a solution of 2.9 g (0.042 mole) of sodium nitrite in 22 ml of 96% strength sulphuric acid is added at 0° C. The mixture is stirred at 0° C. for one hour, and 50 ml of 50% strength hypophosphorous acid are then added dropwise at this temperature. When the addition has ended, the mixture is stirred at 0°–10° C. for three hours and then extracted with 200 ml of methylene chloride. The organic phase is separated off washed with sodium bicarbonate and sodium chloride solution and dried over magnesium sulphate. After the solvent has been evaporated off in vacuo, 14.2 g of a yellow oil are obtained, and are purified by column chromatography with silica gel as the support and methylene chloride as the mobile phase.

5.2 g (36% of theory) of 4-dichloro-fluoromethanesulphenyl-1-(2,6-dichloro-4-trifluoromethylphenyl)-pyrazole of melting point 58° C. are obtained.

Preparation of the starting compound

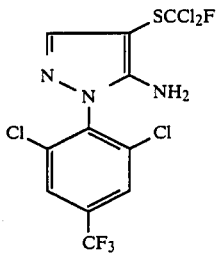

10 g (0.034 mole) of 5-amino-1-(2,6-dichloro-4-trifluoromethyl)-pyrazole are dissolved in 50 ml of glacial acetic acid and 6.1 g (0.036 mole) of dichlorofluoromethanesulphenyl chloride are added dropwise at room temperature. The temperature rises to about 40° C. The reaction mixture is stirred for 2 hours and then introduced into a mixture of 200 ml of water and 50 ml of methylene chloride. The organic phase is separated off and the aqueous phase is extracted with two portions of 20 ml of methylene chloride. The combined organic phases are washed in succession with sodium bicarbonate solution and sodium chloride solution, dried over magnesium sulphate and concentrated in vacuo.

13.6 g (94% of theory) of 5-amino-4-dichloro-fluoromethanesulphenyl-1-(2,6-dichloro-4-trifluoromethylphenyl)-pyrazole of melting point 100° C.–103° C. are obtained.

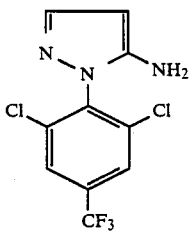

25 ml (27.6 g/0.3 mole) of 2-chloro-acrylonitrile are added dropwise to 24.5 g (0.1 mole) of 2,6-dichloro-4-trifluoromethylphenylhydrazine and with 20 mg of disodium ethylenediamine-tetraacetate (=Titriplex III) in 150 ml of methanol at the reflux temperature. When the addition has ended, the mixture is heated at the reflux temperature for a further 8 hours, 9 ml (0.16 mole) of 96% strength sulphuric acid are then added dropwise and the mixture is heated at the reflux temperature for a further 6 hours.

33.5 g (0.3 mole) of anhydrous sodium carbonate are added to the cooled reaction mixture. After 4 hours, the solvent is removed in vacuo, the residue is taken up in 500 ml of water and the mixture is stirred at room temperature for 10 hours. The precipitate which has separated out is filtered off, rinsed with water and dried in vacuo at 50° C.

28.5 g (96% of theory) of 5-amino-1-(2,6-dichloro-4-trifluoromethylphenyl)-pyrazole of melting point 103° C.–105° C. are obtained.

Example 2

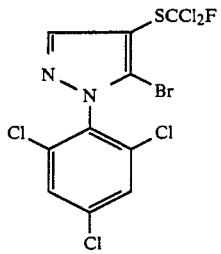

18.0 g (0.046 mole) of 5-amino-4-dichlorofluoromethylmercapto-1-(2,4,6-trichlorophenyl)-pyrazole are dissolved in 60 ml of bromoform, and 13.9 g (0.135 mole) of tert.-butyl nitrite are added at room temperature. The temperature rises to 40°–50° C. during this procedure. The reaction mixture is subsequently stirred for four hours, diluted with 200 ml of methylene chloride and washed in succession with sodium bicarbonate solution, sodium thiosulphate solution and sodium chloride solution. The organic phase is dried over magnesium sulphate and freed from the solvent in vacuo.

19.0 g (91% of theory) of 5-bromo-4-dichlorofluoromethanesulphenyl-1-(2,4,6-trichlorophenyl)-pyrazole of melting point 118° C.–122° C. are obtained.

Preparation of the starting compound

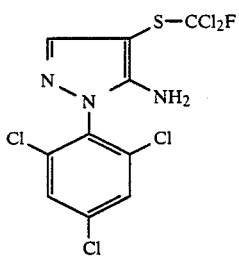

12.6 ml (0.12 mole) of dichlorofluoromethanesulphenyl chloride are added to 30 g (0.114 mole) of 5-amino-1-(2,4,6-trichlorophenyl)-pyrazole and 10 ml (0.125 mole) of anhydrous pyridine in 150 ml of methylene chloride at 0° C. to 5° C. and the mixture is stirred for 30 minutes. For working up, 100 ml of methylene chloride are added, the mixture is washed in succession with dilute hydrochloric acid, water, sodium carbonate solution and sodium chloride solution and dried over magnesium sulphate and the solvent is removed in vacuo.

44.5 g (98.7% of theory) of 5-amino-4-dichlorofluoromethanesulphenyl-1-(2,4,6-tirchlorophenyl)-pyrazole of melting point 101° C. to 106° C. are obtained.

Example 3

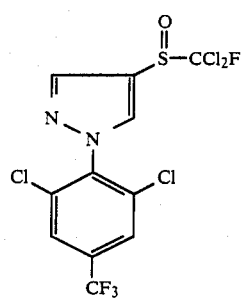

2.1 g (0.005 mole) of 4-dichlorofluoromethanesulphenyl-1-(2,6-dichloro-4-trifluoromethyl-phenyl)-pyrazole are dissolved in 25 ml of methylene chloride and 1.2 g (0.007 mole) of 90% strength m-chloroperbenzoic acid are added at about 10° C. The temperature is allowed to rise to 20° C. in the course of 2 hours and the mixture is then worked up as follows: The m-chlorobenzoic acid which has precipitated out is filtered off and washed with a little methylene chloride. The combined organic phases are washed with sodium bicarbonate solution, sodium thiosulphate solution and again with sodium bicarbonate solution, dried over magnesium sulphate and concentrated in vacuo.

1.9 g (87% of theory) of 4-dichlorofluoromethanesulphinyl-1-(2,6-dichloro-4-trifluoromethyl-phenyl)-pyrazole of melting point 144° C. are obtained.

The following 1-aryl-pyrazoles of the general formula (I) are obtained in a corresponding manner and in accordance with the general statements on the preparation:

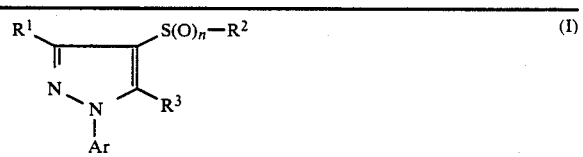

| Example No. | $R^1$ | $R^2$ | $R^3$ | n | Ar | physical data |
|---|---|---|---|---|---|---|
| 4 | H | $CF_3$ | H | 0 | 2,4-dichloro-5-trifluoromethyl-phenyl | $n_D^{20} = 1.4972$ |
| 5 | H | $CCl_2F$ | Br | 0 | 2,4-dichloro-5-bromo-phenyl | Melting point 118° C. |
| 6 | H | $CCl_2F$ | Cl | 0 | phenyl | Boiling point 150° C./0.13 mbar |
| 7 | H | $CCl_2F$ | Cl | 0 | 2,4-dichloro-5-trifluoromethyl-phenyl | Melting point 172–174° C. |
| 8 | H | $CCl_2F$ | Br | 0 | 2,4-dichloro-5-trifluoromethyl-phenyl | Boiling point 145° C./0.013 mbar |
| 9 | H | —$CCl_2F$ | Br | 2 | 2,4-dichloro-5-trifluoromethyl-phenyl | Melting point 104–108° C. |

-continued

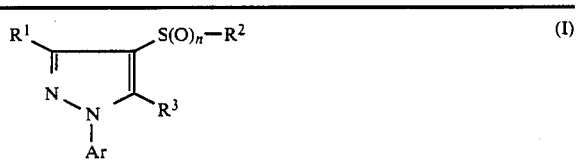

| Example No. | $R^1$ | $R^2$ | $R^3$ | n | Ar | physical data |
|---|---|---|---|---|---|---|
| 10 | H | —CCl$_2$F | Br | 2 | 2,5-dichloro-4-bromo-(CF$_3$)phenyl (Cl, Cl, Br, CF$_3$) | Melting point 78–82° C. |
| 11 | H | —CCl$_2$F | H | 0 | 2,4,5-trichlorophenyl | $n_D^{20} = 1.6188$ |
| 12 | H | —CF$_3$ | Br | 0 | 2,5-dichloro-4-(CF$_3$)phenyl | $n_D^{20} = 1.5200$ |
| 13 | H | —CF$_3$ | Br | 2 | 2,5-dichloro-4-(CF$_3$)phenyl | Melting point 90–91° C. |
| 14 | CH$_3$ | —CCl$_2$F | H | 0 | 2,5-dichloro-4-(CF$_3$)phenyl | $^1$H—NMR* 7.81 ppm |
| 15 | CH$_3$ | —CCl$_2$F | H | 0 | phenyl | $^1$H—NMR* 8.1 ppm |
| 16 | CH$_3$ | —CCl$_2$F | Br | 0 | 2,5-dichloro-4-(CF$_3$)phenyl | Melting point 60–62° C. |
| 17 | CH$_3$ | —CF$_3$ | Br | 0 | 2,5-dichloro-4-(CF$_3$)phenyl | Melting point 68–70° C. |

-continued

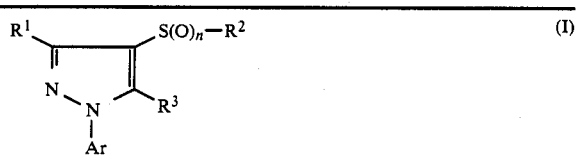

| Example No. | R¹ | R² | R³ | n | Ar | physical data |
|---|---|---|---|---|---|---|
| 18 | CH₃ | —CF₃ | H | 0 | 2,5-dichloro-4-CF₃-phenyl | ¹H—NMR* 7.76 ppm |
| 19 | H | —CF₂Cl | Br | 0 | 2,5-dichloro-4-Br-phenyl | Melting point 99–102° C. |
| 20 | H | —CCl₂F | Br | 0 | 2,5-dichloro-4-Br-phenyl | Melting point 115–118° C. |
| 21 | CH₃ | —CCl₂F | Cl | 0 | 2,5-dichloro-4-CF₃-phenyl | Melting point 63° C. |
| 22 | CH₃ | —CF₃ | Cl | 0 | 2,5-dichloro-4-CF₃-phenyl | Melting point 59° C. |
| 23 | CH₃ | —CF₃ | H | 1 | 2,5-dichloro-4-CF₃-phenyl | Melting point 81° C. |
| 24 | CH₃ | —CCl₂F | H | 1 | 2,5-dichloro-4-CF₃-phenyl | Melting point 100° C. |
| 25 | CH₃ | —CF₃ | Br | 2 | 2,5-dichloro-4-CF₃-phenyl | Melting point 34–86° C. |

-continued
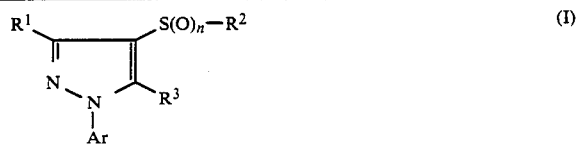
| Example No. | R¹ | R² | R³ | n | Ar | physical data |
|---|---|---|---|---|---|---|
| 26 | $CH_3$ | $-CCl_2F$ | H | 2 | 2,4-Cl, 4-CF₃ phenyl | Melting point 88–91° C. |
| 27 | H | $-CF_3$ | Br | 1 | 2,4-Cl, 4-CF₃ phenyl | Melting point 94–102° C. |
| 28 | H | $-CF_3$ | Br | 0 | 2-Cl, 4-OCF₃ phenyl | $n_D^2 = 1.5010$ |
| 29 | H | $-CCl_2F$ | Br | 2 | 2-Cl, 4,5-Br phenyl | Melting point 125–130° C. |
| 30 | H | $-CCl_2F$ | H | 0 | 2-Cl, 4-CF₃, 5-Br phenyl | viscous oil |
| 31 | H | $-CCl_2F$ | Br | 1 | 2,5-Cl, 4-Br phenyl | Melting point 113–122° C. |
| 32 | H | $-CCl_2F$ | Br | 1 | 2-Cl, 4,5-Br phenyl | Melting point 148–153° C. |
| 33 | H | $-CCl_2F$ | Br | 2 | 2-Cl, 4-CF₃, 5-Br phenyl | Melting point 97–110° C. |

-continued

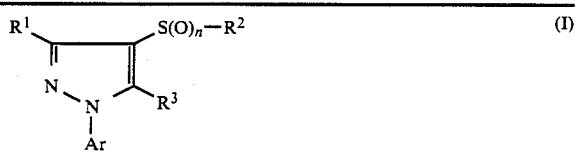

| Example No. | R¹ | R² | R³ | n | Ar | physical data |
|---|---|---|---|---|---|---|
| 34 | H | —CCl$_2$F | Br | 0 | 2,5-dibromo-4-CF$_3$-phenyl (Cl top, Br bottom, CF$_3$ right) | Boiling point 180° C./0.05 mbar |
| 35 | H | —CCl$_2$F | Cl | 0 | 2-Cl, 5-Br, 4-CF$_3$-phenyl | Melting point 183–185° C. |
| 36 | H | —CCl$_2$F | Br | 2 | 2,6-dichloro-4-bromophenyl | Melting point 114–122° C. |
| 37 | H | —CCl$_2$F | Br | 1 | 2-Cl, 5-Br, 4-CF$_3$-phenyl | Melting point 122–134° C. |
| 38 | H | —CCl$_2$F | Br | 0 | 2,6-dimethyl-4-bromophenyl | Melting point 87–92° C. |
| 39 | H | —CH$_3$ | Br | 2 | 2,6-dichloro-4-CF$_3$-phenyl | Melting point 130–132° C. |
| 40 | CH$_3$ | —CF$_3$ | Br | 0 | 2,4-dibromo-6-chlorophenyl | Melting point 101–102° C. |
| 41 | C$_2$H$_5$ | —CCl$_2$F | Br | 0 | 2,4,6-trichlorophenyl | $^1$H—NMR: $\epsilon$ = 7.49 ppm |

-continued

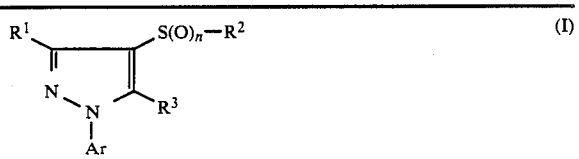

| Example No. | R$^1$ | R$^2$ | R$^3$ | n | Ar | physical data |
|---|---|---|---|---|---|---|
| 42 | C$_2$H$_5$ | —CF$_3$ | Br | 0 | 2,4,6-trichlorophenyl (Cl, Cl, Cl) | $^1$H—NMR: ε = 7.48 ppm |
| 43 | H | —CCl$_2$F | Br | 0 | 3-chloro-5-trifluoromethyl-2-pyridyl | Melting point: 44–46° C. |
| 44 | CH$_3$ | —CCl$_2$F | Br | 1 | 2,6-dichloro-4-trifluoromethylphenyl | Melting point 104–7° C. |
| 45 | CH$_3$ | —CF$_3$ | Br | 1 | 2,6-dichloro-4-trifluoromethylphenyl | Melting point 104° C. |
| 46 | CH$_3$ | —CF$_3$ | H | 2 | 2,6-dichloro-4-trifluoromethylphenyl | Melting point 68–72° C. |
| 47 | CH$_3$ | —CCl$_2$F | Br | 0 | 2-chloro-6-bromo-4-trifluoromethylphenyl | Melting point 35–40° C. |
| 48 | CH$_3$ | —CF$_3$ | Br | 0 | 2-chloro-6-bromo-4-trifluoromethylphenyl | Melting point 66–67° C. |
| 49 | CH$_3$ | —CF$_3$ | Br | 0 | 2,5-dichloro-4-bromophenyl | Melting point 96–97° C. |

-continued

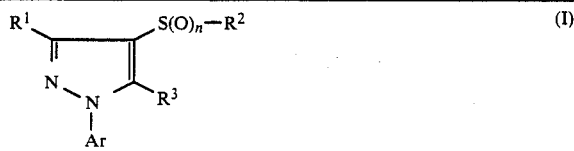

| Example No. | R¹ | R² | R³ | n | Ar | physical data |
|---|---|---|---|---|---|---|
| 50 | $CH_3$ | $-CClF_2$ | Br | 0 | 2,6-dichloro-4-(trifluoromethyl)phenyl | Melting point 57–9° C. |
| 51 | $CH_3$ | $-CCl_2F$ | Br | 0 | 2,6-dichloro-4-(trifluoromethyl)phenyl | Melting point 77–83° C. |
| 52 | $CH_3$ | $-CF_3$ | Br | 0 | 2,4,6-trichlorophenyl | Melting point 83–85° C. |
| 53 | $CH_3$ | $-CCl_2F$ | Br | 0 | 2,4,6-trichlorophenyl | Melting point 83–85° C. |
| 54 | $CH_3$ | $-CClF_2$ | Br | 0 | 2,4,6-trichlorophenyl | Melting point 57–9° C. |
| 55 | $CH_3$ | $-CF_3$ | Br | 0 | 2,6-dichloro-4-(trifluoromethoxy)phenyl | Melting point 48–50° C. |
| 56 | $CH_3$ | $-CCl_2F$ | Br | 0 | 2,6-dichloro-4-(trifluoromethoxy)phenyl | Melting point 85–7° C. |
| 57 | $CH_3$ | $-CClF_2$ | Br | 0 | 2,6-dichloro-4-(trifluoromethoxy)phenyl | Melting point 63–4° C. |

-continued

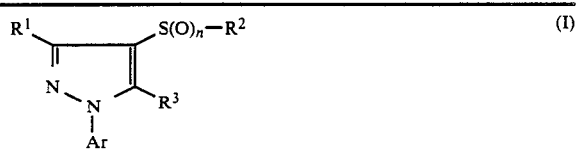

| Example No. | R¹ | R² | R³ | n | Ar | physical data |
|---|---|---|---|---|---|---|
| 58 | $CH_3$ | $-CF_3$ | Br | 2 | 2,4,6-trichlorophenyl (Cl, Cl, Cl) | Melting point 104–06° C. |
| 59 | $CH_3$ | $-CCl_2F$ | Br | 0 | 4-bromo-2,6-dichlorophenyl (Cl, Cl, Br) | Melting point 85–7° C. |
| 60 | $CH_3$ | $-CCl_2F$ | Br | 2 | 2,4,6-trichlorophenyl (Cl, Cl, Cl) | $^1H$—NMR ($CDCl_3$): δ 2.56 (s, 3H), δ 7.50 (m, 2H) |
| 61 | $CH_3$ | $-CClF_2$ | Br | 2 | 2,4,6-trichlorophenyl (Cl, Cl, Cl) | Melting point 81–3° C. |
| 62 | $CH_3$ | $-CF_3$ | Br | 2 | 2,6-dichloro-4-trifluoromethoxyphenyl (Cl, Cl, $OCF_3$) | Melting point 74–6° C. |
| 63 | $CH_3$ | $-CCl_2F$ | Br | 2 | 2,6-dichloro-4-trifluoromethoxyphenyl (Cl, Cl, $OCF_3$) | $^1H$—NMR ($CDCl_3$): δ 2.60 (s, 3H), δ 7.37 (m, 2H) |
| 64 | $CH_3$ | $-CClF_2$ | Br | 2 | 2,6-dichloro-4-trifluoromethoxyphenyl (Cl, Cl, $OCF_3$) | Melting point 88–90° C. |
| 65 | $CH_3$ | $-CClF_2$ | Br | 2 | 2,6-dichloro-4-trifluoromethylphenyl (Cl, Cl, $CF_3$) | Melting point 77–9° C. |

-continued $$\text{(I)}$$

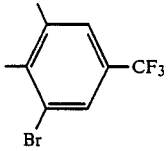

| Example No. | R¹ | R² | R³ | n | Ar | physical data |
|---|---|---|---|---|---|---|
| 66 | CH₃ | —CClF₂ | Br | 0 | 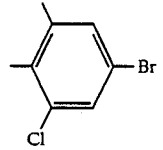 2-Cl, 4-CF₃, 6-Br (methyl) | Melting point 74–75° C. |
| 67 | CH₃ | —CCl₂F | Br | 0 | 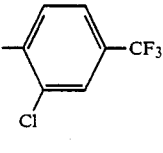 2,6-diCl, 4-Br (methyl) | Melting point 70–1° C. |
| 68 | CH₃ | —CClF₂ | Br | 0 | 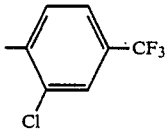 2-Cl, 4-CF₃ (methyl) | Melting point 61–2° C. |
| 69 | CH₃ | —CClF₂ | Br | 0 | 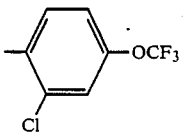 2-Cl, 4-CF₃ (methyl) | Melting point 40–50° C. ¹H—NMR (CDCl₃) δ 2.47 (s, 3H) |
| 70 | CH₃ | —CF₃ | Br | 0 | 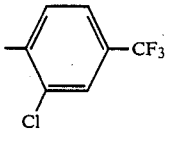 2-Cl, 4-OCF₃ (methyl) | Melting point 40–45° C. ¹H—NMR (CDCl₃) δ 2.45 (3H, s) |
| 71 | CH₃ | —CCl₂F | H | 0 | 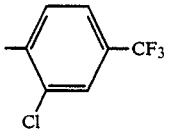 2-Cl, 4-CF₃ (methyl) | ¹H—NMR (CDCl₃) δ 2.48 (s, 3H) δ 7.68 (d, v, d, 1H) δ 8.85 (d, v, d, 2H) δ 8.29 (s, 1H) |
| 72 | CH₃ | —CClF₂ | H | 0 | 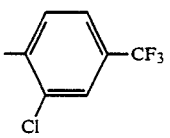 2-Cl, 4-CF₃ (methyl) | ¹H—NMR (CDCl₃) δ 2.42 (s, 3H) δ 7.69 (d, v, d, 1H) δ 7.84 (2H) δ 7.25 (s, 1H) |
| 73 | CH₃ | —CF₃ | H | 0 | 2-Cl, 4-CF₃ (methyl) | ¹H—NMR (CDCl₃) δ 2.43 (s, 3H) δ 7.67 (d, v, d, 1H) δ 7.82 (m, 2H) δ 8.24 (s, 1H) |
| 74 | H | —CCl₂F | Br | 0 | 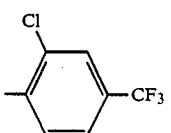 2,4-diCl, 6-CF₃ | ¹H—NMR (CDCl₃) δ 8.04 (s, 1H) |

-continued

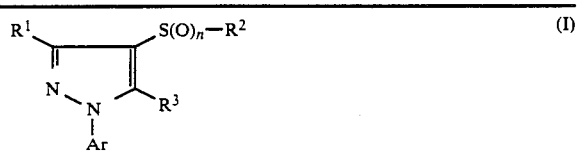
(I)

| Example No. | R¹ | R² | R³ | n | Ar | physical data |
|---|---|---|---|---|---|---|
| 75 | H | —CCl₂F | H | 2 | 2,6-dichloro-4-(trifluoromethyl)phenyl | Melting point 145–155° C. |
| 76 | H | —CF₃ | Br | 0 | 2,4,6-trichlorophenyl | Melting point 75–78° C. |
| 77 | H | —CF₃ | Br | 0 | 4-bromo-2,6-dichlorophenyl | Melting point 62–66° C. |
| 78 | H | —CCl₂F | Br | 1 | 2,6-dichloro-4-(trifluoromethyl)phenyl | Melting point 125–28° C. |
| 79 | H | —CClF₂ | H | 0 | 2,6-dichloro-4-(trifluoromethyl)phenyl | $^1$H—NMR (CDCl₃) δ 7.87 (s, 1H) δ 7.98 (s, 1H) |
| 80 | H | —CF₃ | H | 1 | 2,6-dichloro-4-(trifluoromethyl)phenyl | Melting point 102–03° C. |
| 81 | H | —CClF₂ | H | 1 | 2,6-dichloro-4-(trifluoromethyl)phenyl | Melting point 126–27° C. |
| 82 | H | —CF₃ | Br | 0 | 2,6-dichloro-4-(trifluoromethoxy)phenyl | $n_D^{20}$: 1.5090 |

-continued $$\begin{array}{c} R^1 \quad S(O)_n-R^2 \\ \diagdown \diagup \\ N-N \\ | \quad R^3 \\ Ar \end{array} \quad (I)$$

| Example No. | R¹ | R² | R³ | n | Ar | physical data |
|---|---|---|---|---|---|---|
| 83 | H | —CF₃ | H | 2 | 2,6-dichloro-4-(trifluoromethyl)phenyl | Melting point 108–09° C. |
| 84 | H | —CCl₂F | Br | 0 | 2-bromo-6-chloro-4-fluorophenyl | ¹H—NMR (CDCl₃) δ 7.98 (s, 1H) |
| 85 | H | —CF₂Cl | Br | 0 | 2-bromo-6-chloro-4-(trifluoromethyl)phenyl | ¹H—NMR (CDCl₃) δ 8.03 (s, 1H) |
| 86 | H | —CClF₂ | Br | 0 | 2,6-dibromo-4-(trifluoromethyl)phenyl | Boiling point 175° C./0,05 mbar |
| 87 | H | —CClF₂ | Br | 2 | 2,6-dibromo-4-(trifluoromethyl)phenyl | Melting point 90–100° C. |
| 88 | H | —CClF₂ | Br | 0 | 2,6-dichloro-4-(trifluoromethoxy)phenyl | Boiling point 160° C./0,01 mbar |
| 89 | H | —CCl₂F | Br | 0 | 2-bromo-6-chloro-4-bromo... | Melting point 124–27° C. |
| 90 | H | —CCl₂F | Br | 0 | 2-bromo-6-chloro-4-bromo... | Melting point 116–20° C. |

-continued

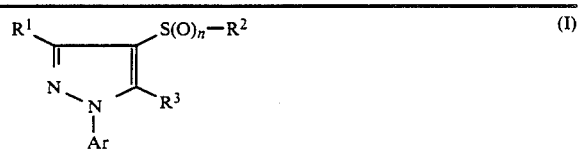

| Example No. | R¹ | R² | R³ | n | Ar | physical data |
|---|---|---|---|---|---|---|
| 91 | H | —CCl₂F | Br | 2 | 3,5-dichloro-4-methyl-(OCF₃) phenyl | Melting point 57–61° C. |
| 92 | H | —CCl₂F | Br | 1 | 2-bromo-4-CF₃-phenyl | Melting point 110–120° C. |
| 93 | H | —CClF₂ | Br | 1 | 3,5-dichloro-4-methyl-(OCF₃) phenyl | Melting point 92–95° C. |
| 94 | H | —CCl₂F | Br | 2 | 2-bromo-4-CF₃-phenyl | ¹H—NMR (CDCl₂) δ 8.25 (s, 1H) |
| 95 | H | —CCl₂F | Br | 0 | 2-chloro-4-CF₃-phenyl | Boiling point 150° C./0.02 mbar |
| 96 | H | —CF₃ | H | 0 | 2,6-dibromo-4-CF₃-phenyl | ¹H—NMR (CDCl₃) δ 7.76 (d, 1H) δ 7.88 (d, 3H) |
| 97 | H | —CCl₂F | H | 0 | 2,6-dibromo-4-CF₃-phenyl | Melting point 69–71° C. |
| 98 | H | —CF₂Cl | Br | 2 | 2,6-dichloro-4-bromo-phenyl | Melting point 90–39° C. |
| 99 | H | —CF₂Cl | H | 0 | 2-bromo-4-CF₃-phenyl | Boiling point 140° C./0.01 mbar |

-continued

| Example No. | $R^1$ | $R^2$ | $R^3$ | n | Ar | physical data |
|---|---|---|---|---|---|---|
| 100 | H | 4-chlorophenyl | Br | 2 | 2,6-dichloro-4-(trifluoromethyl)phenyl | Melting point 164–67° C. |
| 101 | H | —CH$_3$ | H | 0 | 2,6-dichloro-4-(trifluoromethyl)phenyl | $n_D^{20}$: 1.5525 |
| 102 | CH$_3$ | —CH$_3$ | H | 0 | 2,6-dichloro-4-(trifluoromethyl)phenyl | $n_D^{20}$: 1.5519 |

*The $^1$H—NMR spectra were recorded in CDCl$_3$ with tetramethylsilane as the internal standard. The chemical shift (as the δ value) of the hydrogen atom in the 5-position of the pyrazole ring is stated

Use Examples

The compounds shown below were employed as comparison substances in the following use examples:

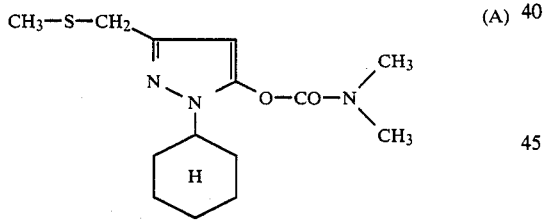

1-Cyclohexyl-5-[N,N-(dimethyl)-carbamyloxy]-3-methylthiomethyl-pyrazole (known from DE-OS (German Published Specification) No. 2,839,270)

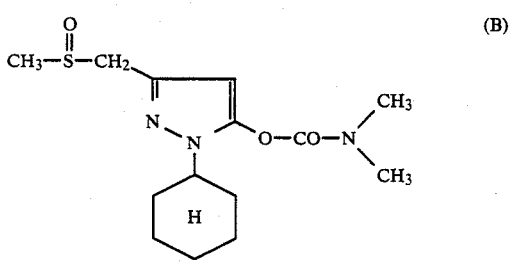

1-Cyclohexyl-5-[N,N-(dimethyl)-carbamyloxy]-3-methylsulphinylmethyl-pyrazole (known from DE-OS (German Published Specification) No. 2,839,270)

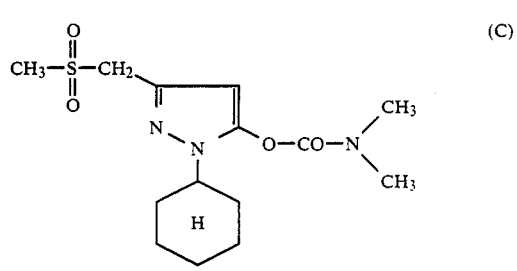

1-Cyclohexyl-5-[N,N-(dimethyl)-carbamyloxy]-3-methylsulphonylmethyl-pyrazole (known from DE-OS (German Published Specification) No. 2,839,270).

Example A

Phaedon larvae test

Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of the active compound of the desired concentration and are infested with mustard beetle larvae (*Phaedon cochleariae*), as long as the leaves are still moist.

After the specified period of time, the destruction in % is determined. 100% means that all the larvae have been killed; 0% means that none of the larvae has been killed.

In this test, for example, the following compounds from the preparation examples show a superior activity compared to the prior art: 1, 5, 7, 11, 14, 16, 4, 28, 12, 18, 17, 40, 27, 13, 39, 37, 10, 36, 29, 2, 19, 34, 20, 35 and 46.

Example B

Tetranychus test (resistant)

Solvent: 7 parts by weight of dimethylformamide

Emulsifier: 1 part by weight of alkylaryl polyglycol ether.

To produce a suitable preparation of active compound, 1 part by weight of active compound is mixed with the stated amount of solvent and the stated amount of emulsifier, and the concentrate is diluted with water to the desired concentration.

Bean plants (*Phaseolus vulgaris*) which are heavily infested with the common spider mite or two-spotted spider mite (*Tetranychus urticae*) in all stages of development are treated by being dipped into the preparation of the active compound of the desired concentration.

After the specified period of time, the destruction in % is determined. 100% means that all the spider mites have been killed; 0% means that none of the spider mites has been killed.

In this test, for example, the following compounds from the preparation examples show a superior activity compared to the prior art: 1, 5, 14, 38, 2, 34, 10, 20 and 36.

Example C

Test insect: *Phorbia antiqua* maggots (in the soil)

Solvent: 3 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil. The concentration of the active compound in the preparation is of practically no importance, only the amount by weight of active compound per unit volume of soil, which is given in ppm (=mg/liter) being decisive. The soil is filled into pots and the pots are left to stand at room temperature.

After 24 hours, the test insects are introduced into the treated soil, and after a further 2 to 7 days the degree of effectiveness of the active compound is determined in % by counting the dead and live test insects. The degree of effectiveness is 100% if all the test insects have been killed and is 0% if just as many test insects are still alive as in the case of the untreated control.

In this test, for example, the following compounds from the preparation examples show a superior action compared with the prior art: 1, 14 and 16.

Example D

LT$_{100}$ test for Diptera

Test insects: *Musca domestica* (resistant)

Number of test insects: 25

Solvent: Acetone 2 parts by weight of active compound are taken up in 1,000 parts by volume of solvent. The solution thus obtained is diluted with further solvent to the desired lower concentrations.

2.5 ml of the active compound solution are pipetted into a Petri dish. A filterpaper disc of about 9.5 cm diameter is located on the bottom of the Petri dish. The Petri dish is left standing open until the solvent has completely evaporated. The amount of active compound per m$^3$ of filterpaper varies, depending on the concentration of the active compound solution. The stated number of test insects is then introduced into the Petri dish, and the dish is covered with a glass lid.

The condition of the tests insects is checked continuously. The time required for a 100% knock-down effect is determined.

In this test, for example, the following compounds from the preparation examples show a superior action compared to the prior art: 1, 8, 14 and 16.

Example E

Test insects: *Sitophilus granarius*

Number of test insects: 25

Solvent: Acetone 2 parts by weight of active compound are taken up in 1,000 parts by volume of solvent. The solution thus obtained is diluted with further solvent to the desired concentrations.

2.5 ml of the active compound solution are pipetted into a Petri dish. A filterpaper disc of about 9.5 cm diameter is located on the bottom of the Petri dish. The Petri dish is left standing open until the solvent has completely evaporated. The amount of active compound per m$^3$ of filterpaper varies, depending on the concentration of the active compound solution. The stated number of test insects is then introduced into the Petri dish, and the dish is covered with a glass lid.

The condition of the test insects is checked 3 days after the test has been set up. The destruction in % is determined. 100% means that all the test insects have been killed; 0% means that none of the test insects has been killed.

In this test, for example, the following compounds from the preparation examples show a superior action compared to the prior art: 1, 7, 8, 11, 14, 16, 46, 79, 83 and 102.

Example F

Test insects: *Leucophaea maderae*

Number of test insects: 25

Solvent: Acetone 2 parts by weight of active compound are taken up in 1,000 parts by volume of solvent. The solution thus obtained is diluted with further solvent to the desired concentrations.

2.5 ml of the active compound solution are pipetted into a Petri dish. A filterpaper disc of about 9.5 cm diameter is located on the bottom of the Petri dish. The Petri dish is left standing open until the solvent has completely evaporated. The amount of active compound per m$^3$ of filterpaper varies, depending on the concentration of the active compound solution. The stated number of test insects is then introduced into the Petri dish, and the dish is covered with a glass lid.

The condition of the test insects is checked 3 days after the test has been set up. The destruction in % is determined. 100% means that all the test insects have been killed; 0% means that none of the test insects has been killed.

In this test, for example, the following compounds from the preparation examples show a superior action compared to the prior art: 1, 8, 14, 46, 79, 83 and 102.

Example G

Test with *Lucilia cuprina* res. larvae
(OP-resistant Goondiwindi strain)

Emulsifier: 35 parts by weight of ethylene glycol monomethyl ether; 35 parts by weight of nonylphenol polyglcol ether.

To produce a suitable preparation of active compound, three parts by weight of active compound are mixed with seven parts by weight of the abovementioned solvent mixture and the concentrate thus obtained is diluted with water to the particular desired concentration.

About 20 *Lucilia cuprina* res. larvae are introduced into a test tube which contains approx. 1 cm$^3$ of horse muscle and 0.5 ml of the preparation of active compound. After 24 hours, the degree of destruction is determined.

In this test, for example, the following compounds from the preparation examples show a superior action compared to the prior art: 1, 8 and 14.

Example H

Test with parasitic, adult biting flies (*Stomoxys calcitrans*)

Solvent: Cremophor

To produce a suitable preparation of active compound, the active substance in question is mixed with the stated solvent in a ratio of 1:2 and the concentrate thus obtained is diluted with water to the desired concentration.

10 adult biting flies (*Stomoxys calcitrans*) are introduced into Petri dishes containing sandwiches which have been impregnated one day before the start of the test with 1 ml of the active compound preparation to be tested. After 3 hours, the degree of destruction is determined in percent, 100% meaning that all the flies have been killed and 0% meaning that none of the flies has been killed.

In this test, for example, the following compounds from the preparation examples show a superior action compared to the prior art: 1 and 7.

Example I $LD_{100}$-Test
Test insects: *Blatella germanica*
Solvent: Acetone 2 parts by weight of active compound are taken up in 1,000 parts by volume of the solvent. The solution thus obtained is diluted with further solvent to the desired concentrations.

2.5 ml of the solution of active compound are pipetted into a Petri dish. On the bottom of the Petri dish there is a filter paper with a diameter of about 9.5 cm. The Petri dish remains uncovered until the solvent has completely evaporated. The amount of active compound per m$^2$ of filter paper varies with the concentration of the solution of active compound. Approximately 10 test insects are then placed in the Petri dish and the dish is covered with a glass lid.

The condition of the test insects is checked 3 days after the commencement of the experiments. The destruction in % is determined.

In this test, for example, the compounds of the following examples showed a destruction of 100% at a maximum concentration of 0.2%: 18, 22, 21, 23, 45, 25, 46, 48, 50, 55, 62, 65, 66, 71, 73, 12, 4, 74, 27, 79, 82, 83, 34, 30, 85, 88, 95, 97, 99, 101, 102, 80, 96.

It will be understood that the specification and examples are illustrative but not limitative of the present invention and that other embodiments within the spirit and scope of the invention will suggest themselves to those skilled in the art.

We claim:

1. A 1-aryl-pyrazole of the formula

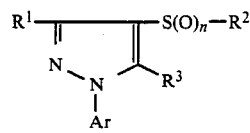

in which
$R^1$ represents hydrogen or $C_1$-$C_4$ alkyl,
$R^2$ represents $C_1$-$C_8$ alkyl or $C_1$-$C_8$ halogenoalkyl,
$R^3$ represents halogen,
Ar represents phenyl which is mono-, di-, tri-, tetra- or pentasubstituted by identical or different substituents selected from the group consisting of fluorine, chlorine, bromine, methyl, ethyl, trifluoromethyl and trifluoromethoxy, and
n represents the number 0, 1 or 2.

2. A 1-aryl-pyrazole according to claim 1, in which
$R^1$ represents hydrogen, or represents in each case straight-chain or branched $C_1$ to $C_4$ alkyl,
$R^2$ represents in each case straight-chain or branched $C_1$ to $C_4$ alkyl or halogenoalkyl with 1 to 8 carbon atoms and 1 to 17 identical or different halogen atoms,
$R^3$ represents fluorine, chlorine, bromine or iodine, and
n represents the number 0, 1 or 2.

3. A 1-aryl-pyrazole according to claim 1,
in which
$R^1$ represents hydrogen, methyl, or ethyl, n-propyl or i-propyl,
$R^2$ represents methyl, ethyl, n- or i-propyl, n-, i-, s- or t-butyl, n- or i-pentyl, n- or i-hexyl, chloromethyl, difluoromethyl, difluorochloromethyl, fluorodichloromethyl, trifluoromethyl, pentafluoroethyl, pentachloroethyl, fluorotetrachloroethyl, difluorotrichloroethyl, trifluorodichloroethyl, tetrafluorochloroethyl, heptafluoropropyl, chloroethyl, bromoethyl, chloropropyl or bromopropyl,
$R^3$ represents fluorine, chlorine or bromine, and
n represents the number 0, 1 or 2.

4. A compound according to claim 1, wherein such compound is 5-bromo-4-dichlorofluoromethanesulphenyl-1-(2,4,6-trichlorophenyl)-pyrazole of the formula

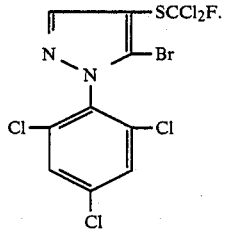

5. A compound according to claim 1, wherein such compound is 5-bromo-4-trifluoromethylsulphenyl-1-(2,6-dichloro-4-trifluoromethyl-phenyl)-pyrazole of the formula

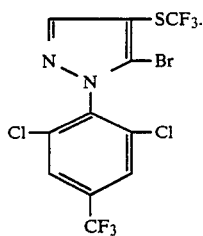

6. A compound according to claim 1, wherein each compound is 5-bromo-4-dichlorofluoromethylsulphenyl-1-(4-bromo-2,6-dichloro-phenyl)-pyrazole of the formula

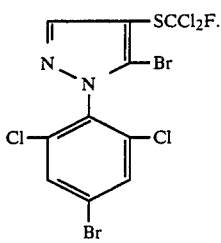

7. A compound according to claim 1, wherein such compound is 5-bromo-4-dichlorofluoromethylsulphonyl-1-(4-bromo-2,6-dichloro-phenyl)-pyrazole of the formula

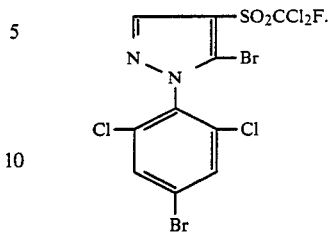

8. An insecticidal or acaricidal composition comprising an insecticidally or acaricidally effective amount of a compound according to claim 1 and a diluent.

9. A method of combating insects or acarids which comprises applying to such insects, acarids or a habitat thereof an insecticidally or acaricidally effective amount of a compound according to claim 1.

10. The method according to claim 8, wherein such compound is
5-bromo-4-dichlorofluoromethanesulphenyl-1-(2,4,6-trichlorophenyl)-pyrazole,
5-bromo-4-trifluoromethyl-sulphenyl-1-(2,6-dichloro-4-trifluoromethyl-phenyl)-pyrazole,
5-bromo-4-dichlorofluoromethylsulphenyl-1-(4-bromo-2,6-dichloro-phenyl)-pyrazole or
5-bromo-4-dichlorofluoromethylsulphonyl-1-(4-bromo-2,6-dichloro-phenyl)-pyrazole.

* * * * *